United States Patent [19]

Dickinson et al.

[11] Patent Number: 5,086,130
[45] Date of Patent: Feb. 4, 1992

[54] POLY(ARYL ETHER SULFONE) COMPOSITIONS COMPRISING POLY(PHENYLENE ETHER SULFONE)

[75] Inventors: Barry L. Dickinson, Whitehouse Station; M. J. El-Hibri, Highland Park; Marvin E. Sauers, Belle Mead, all of N.J.

[73] Assignee: Amoco Corporation, Chicago, Ill.

[21] Appl. No.: 505,827

[22] Filed: Apr. 6, 1990

Related U.S. Application Data

[63] Continuation-in-part of Ser. No. 163,781, Mar. 3, 1988, abandoned.

[51] Int. Cl.⁵ .................. C06H 283/00; C02G 15/00; C02L 21/00
[52] U.S. Cl. .................. 525/537; 525/934; 525/535
[58] Field of Search .................. 525/534, 535, 537

[56] References Cited

U.S. PATENT DOCUMENTS

| | | | |
|---|---|---|---|
| 3,536,657 | 10/1970 | Noshay et al. | 525/534 |
| 3,783,091 | 1/1974 | Leslie et al. | 525/534 |
| 4,256,862 | 3/1981 | Binsack et al. | 525/534 |
| 4,616,070 | 10/1986 | Ziener et al. | 525/535 |
| 4,743,645 | 5/1988 | Harris et al. | 525/534 |
| 4,804,723 | 2/1989 | Harris et al. | 525/534 |
| 4,818,803 | 4/1989 | Harris | 525/535 |
| 4,957,978 | 9/1990 | Harris | 525/535 |

*Primary Examiner*—John C. Bleutge
*Assistant Examiner*—W. R. H. Clark
*Attorney, Agent, or Firm*—William H. Magidson; Ralph C. Medhurst

[57] ABSTRACT

A poly(aryl ether sulfone) blend comprising (a) from about 25 to about 99 percent by weight of a poly(biphenyl ether sulfone) and (b) from about 1 to about 75 percent by weight of a second poly(phenylene ether sulfone).

5 Claims, No Drawings

POLY(ARYL ETHER SULFONE) COMPOSITIONS COMPRISING POLY(PHENYLENE ETHER SULFONE)

This application is a continuation-in-part of application Ser. No. 163,781, filed Mar. 3, 1988, now abandoned in the name of Sauers et al.

FIELD OF THE INVENTION

This invention is directed to immiscible poly(aryl ether sulfone) blends possessing improved properties comprising (a) from about 25 to about 99 percent by weight of a poly(biphenyl ether sulfone) preferably 60 to 99 percent by weight and (b) from about 1 to about 75 percent by weight of a second poly(phenylene ether sulfone) preferably 40 to 1 weight percent. The compositions described herein, particularly the preferred compositions, retain the very attractive characteristics of their constituents, and display excellent mechanical properties and heat resistance.

Articles made from these poly(aryl ether sulfones) can be steam-sterilized while under stresses of 500 psi or greater; moreover they are not affected by corrosion-reducing additives such a morpholine, for example. Also, the above materials demonstrate good chemical resistance in contact with commonly used hospital cleaners and detergents.

BACKGROUND OF THE INVENTION

Poly(aryl ether sulfones) have been known for about two decades. They are tough linear polymers that possess a number of attractive features such as excellent high temperature resistance, good electrical properties, and very good hydrolytic stability. At least three poly(aryl ether sulfones) are commercially available. A poly(aryl ether sulfone) referred to herein as poly(phenylene ether sulfone) is available from Imperial Chemical Industries, Ltd. It has the formula (1)

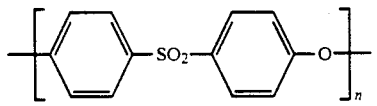
(1)

and is produced by the polycondensation of 4,4'-dihydroxydiphenyl sulfone with 4,4'-dichlorodiphenyl sulfone as described in, for example, Canadian Patent No. 847,963. The polymer contains no aliphatic moieties and has a Tg of approximately 220° C.

Another commercial poly(aryl ether sulfone) is available from Amoco Performance Products, Inc., under the trademark of UDEL®. It corresponds to formula (2),

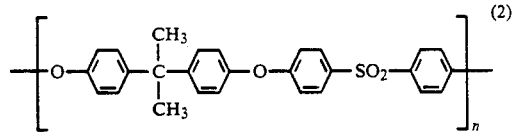
(2)

has a Tg of about 190° C., and is made via the nucleophilic polycondensation of bisphenol-A di-sodium salt with 4,4'-dichlorodiphenyl sulfone, as described in U.S. Pat. No. 4,108,837.

A third commercial poly(aryl ether sulfone) is also available from Amoco Performance Products, Inc., under the trademark of Radel® R. It corresponds to formula (3) has a Tg of about 220° C., and is produced by the polycondensation of biphenol with 4,4'-dichlorodiphenyl sulfone as described in, for example, Canadian Patent No. 847,963.

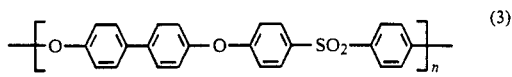
(3)

Over the years, there has developed a substantial body of patent and other literature directed to the formation and properties of poly(aryl ether sulfones and other poly(aryl ethers) (all hereinafter called "PAE"). A broad range of PAE's was achieved by Johnson et al., J. of Polymer Science, A-1, Vol. 5, 1967, pp. 2415-2427; Johnson et al., U.S. Pat. Nos. 4,108,837 and 4,175,175. Johnson et al. show that a very broad range of PAE's can be formed by the nucleophilic aromatic substitution (condensation) reaction of an activated aromatic dihalide and an aromatic diol. By this method, Johnson et al. created a host of new PAE's.

Because of their excellent mechanical and thermal properties, coupled with outstanding hydrolytic stability, the poly(aryl ether sulfones) have been utilized in the medical market for a variety of purposes for at least ten years. These medical devices constitute a wide variety of articles. Obviously one of the major attributes of the poly(aryl ether sulfones) is their ability to be steam autoclaved repeatedly without loss of properties. Steam autoclaving is a very severe test, requiring both high temperature and hydrolytic stability, and involving cyclical effects—wet/dry, hot/cold.

The poly(aryl ether sulfones) (1) and (2) show some important deficiencies, however. Indeed, parts molded from these materials ,stress-crack when steam sterilized under stresses of say 500 psi or greater especially when excessive concentration of boiler additives, such as morpholine are employed to reduce corrosion in the steam generating system; or, when in contact with commonly used hospital cleaners and detergents.

While poly(biphenyl ether sulfone) (3) and parts molded therefrom have substantially better properties than poly(aryl ether sulfones) (1) and (2) it is substantially more expensive than (1) and (2) due to the high cost of biphenol.

British Patent Application No. 2,088,396 describes copolymers containing units (4) and (5):

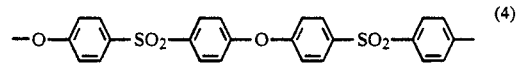
(4)

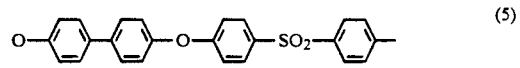
(5)

The claimed copolymers comprise about 80 to 10 mole percent of repeat units (4), and correspondingly about 20 to 90 mole percent of repeat units (5). The application states that the incorporation of (5) into the poly(aryl ether sulfone) (1) yields materials with improved resistance to hot water crazing. The application does not mention steam-sterilizability under load; nor does it teach that the copolymers show resistance to stress-cracking in the presence of boiler additives such as morpholine.

The general object of this invention is to provide blends of poly(biphenyl ether sulfones) having many of the base properties of the poly(biphenyl ether sulfone). Another object of this invention is to provide medical articles from blends of poly(biphenyl ether sulfones) which can be steam-sterilized while under stresses of 500 psi or greater without stress-cracking even in the presence of morpholine. Other objects appear hereinafter.

The general objects of this invention can be attained with immiscible blends comprising (a) from about 25 to about 99 percent by weight of a poly(biphenyl ether sulfone) and (b) from about 1 to 75 percent of weight of a poly(phenylene ether sulfone). Other things being equal blends of polyarylether (1) and poly(aryl ether sulfone) (3) wherein poly(aryl ether sulfone) (3) comprises at least 60% of the two polymers have substantially the same properties as the more expensive poly(aryl ether sulfone) (3). The two polymers can also be used in weight percent ratios of poly(biphenol ether sulfone) of from about 50 to 99 to poly(phenylene ether sulfone) of about 50 to 1 weight percent.

Briefly, the poly(biphenyl ether sulfones) useful in this invention comprise the repeating unit

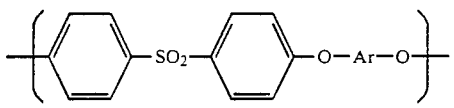

wherein at least 50 and preferably at least 75 mole percent of the divalent Ar groups are p-biphenylene groups and the remainder (0 to 50 mole percent) at least one member selected from the group consisting of p-phenylene,

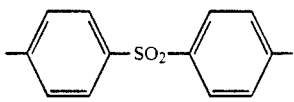

etc. In general, the higher the concentration of biphenyl or biphenylene groups the better the properties of the polymer.

The poly(phenylene ether sulfones) useful in this invention comprise the repeating unit

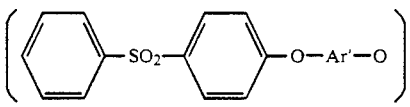

wherein at least 50 and preferably at least 75 mole percent of the divalent Ar' groups are bisphenol S moieties

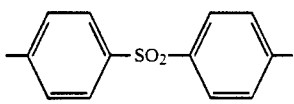

and the remainder (0 to 50 mole percent) p-phenylene.

The poly(aryl ether sulfones) can be prepared by either of two methods, i.e., the carbonate method or the alkali metal hydroxide method.

In the carbonate method, the polymers are prepared by contacting substantially equimolar amounts of the hydroxy-containing compounds and dihalodiarylsulfones, e.g., 4,4'-dichlorodiphenyl sulfone or 4,4'-dichlorodiphenyl sulfone, with from about 0.5 to about 1.0 mole of an alkali metal carbonate per mole of hydroxyl group in a solvent mixture comprising a solvent which forms an azeotrope with water in order to maintain the reaction medium at substantially anhydrous conditions during the polymerization.

The temperature of the reaction mixture is kept at about 170° C. to about 250° C., preferably from about 210° C. to about 235° C. for about one to 15 hours.

The reaction is carried out in an inert atmosphere, e.g., nitrogen, at atmospheric pressure, although higher or lower pressures may also be used.

The polyarylethersulfone is then recovered by conventional techniques such as coagulation, solvent evaporation, and the like.

The solvent mixture comprises a solvent which forms an azeotrope with water and a polar aprotic solvent. The solvent which forms an azeotrope with water includes an aromatic hydrocarbon such as benzene, toluene, xylene, ethylbenzene, chlorobenzene, and the like.

The polar aprotic solvents employed in this invention are those generally known in the art for the manufacture of polyarylether sulfones and include sulfur containing solvents such as those of the formula:

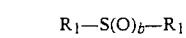

in which each $R_1$ represents a monovalent lower hydrocarbon group free of aliphatic unsaturation, which preferably contains less than about 8 carbon atoms or when connected together represents a divalent alkylene group with b being an integer from 1 to 2 inclusive. Thus, in all of these solvents, all oxygens and two carbon atoms are bonded to the sulfur atom. Contemplated for use in this invention are such solvents as those having the formula:

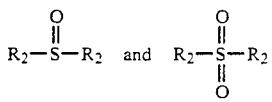

where the $R_2$ groups are independently lower alkyl, such as methyl, ethyl, propyl, butyl, and like groups, and aryl groups such as phenyl and alkylphenyl groups such as the tolyl group, as well as those where the $R_2$ groups are interconnected as in a divalent alkylene bridge such as

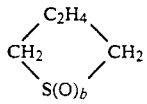

in tetrahydrothiophene oxides and dioxides. Specifically, these solvents include dimethylsulfoxide, dimethylsulfone, diphenylsulfone, diethylsulfoxide, diethylsulfone, diisopropylsulfone, tetrahydrothiophene 1,1-dioxide (commonly called tetramethylene sulfone or sulfolane) and tetrahydrothiophene-1 monoxide.

Additionally, nitrogen containing solvents may be used. These include dimethylacetamide, dimethylformamide and N-methylpyrrolidone.

The azeotrope forming solvent and polar aprotic solvent are used in a weight ratio of from about 1:10 to about 1:1, preferably from about 1:5 to about 1:3.

In the reaction, the hydroxy containing compound is slowly converted, in situ, to the alkali salt thereof by reacting with the alkali metal carbonate. The alkali metal carbonate is preferably potassium carbonate. As indicated before, mixtures of carbonates such as potassium and sodium carbonate may also be used.

Water is continuously removed from the reaction mass as an azeotrope with the azeotrope forming solvent so that substantially anhydrous conditions are maintained during the polymerization.

It is essential that the reaction medium be maintained substantially anhydrous during the polycondensation. While amounts of water up to about one percent can be tolerated, and are somewhat beneficial when employed with fluorinated dihalobenzenoid compounds, amounts of water substantially greater than this are desirably avoided as the reaction of water with the halo and/or nitro compound leads to formation of phenolic species and only low molecular weight products are secured. Consequently, in order to secure the higher polymers, the system should be substantially anhydrous, and preferably contain less that 0.5 percent by weight water during the reaction.

Preferably, after the desired molecular weight has been attained, the polymer is treated with an activated aromatic halide or an aliphatic halide such as methyl chloride or benzyl chloride, and the like. Such treatment of the polymer converts the terminal hydroxyl groups into ether groups which stabilize the polymer. The polymer so treated has good melt and oxidative stability.

While the carbonate method for preparing the polymer of this invention is simple and convenient, in some cases products of higher molecular weight can be made by the alkali metal hydroxide method. In the alkali metal hydroxide method, described by Johnson et al., U.S. Pat. Nos. 4,108,837 and 4,175,175, a double alkali metal salt of a dihydric phenol is contacted with a dihalobenzenoid compound in the presence of a sulfur containing solvent as herein above defined under substantially anhydrous conditions.

Additionally, the polymers of this invention ca be prepared by other methods known in the prior art, in which at least one dihydric phenol and at least one dihalobenzenoid compound are heated, for example, with a mixture of sodium carbonate or bicarbonate and a second alkali metal carbonate or bicarbonate having a higher atomic number than that of sodium, as described in U.S. Pat. No. 4,176,222.

The molecular weight of the poly(aryl ethers) utilized for manufacturing the devices of the instant invention is indicated by reduced viscosity data in an appropriate solvent such as methylene chloride, chloroform, N,methylpyrrolidone, and the like. The reduced viscosities of the materials, as measured at concentrations of 0.2 g per 100 ml. at 25° C., are at least 0.3 dl/g, preferably at least 0.4 dl/g and, typically, not exceeding about 1.5 dl/g.

The compositions of this invention are prepared by any conventional mixing method. For example, a preferred method comprises mixing the two poly(aryl ether sulfones) in powder or pellets form in an extruder and extruding the mixture into strands, chopping the strands into pellets and molding the pellets into the desired article.

The poly(aryl ether sulfones) of the instant invention allow for the fabrication of medical devices having outstanding stress-crack resistance. These devices can be steam-sterilized under stresses of 500 psi or greater and in the presence of a variety of steam boiler additives. Typical boiler additives designed to reduce corrosion in steam generating systems are amino compounds such as morpholine, hydrazine, N,N-diethylaminoethanol ("NALCO 359" or "BETZ NA-9"), and octadecylamine, Steam sterilization is also possible in the presence of various hospital cleaners and detergents, such as those sold under the tradenames of "Castle 7900" (a sonic cleaner), "Chem Crest 14" (an ultrasonic cleaner), "Tergitol Min Foam 2X" (a non ionic surfactant), and the like.

The materials of the instant invention can include pigments, thermal stabilizers, ultraviolet light stabilizer, and other additives.

The instant poly(aryl ether sulfones) blends are useful for the fabrication of a wide variety of medical devices. They are of particular interest for autoclavable storage trays such as the systems for storage and delivery of sterile surgical instruments (thus eliminating the costs associated with wrapping); in the medical supply industry for shipment and storage of implants, prostheses and other medical devices under sterile conditions; and in many other similar applications.

The compositions of this invention can also be fabricated into any desired shape, i.e., moldings, coatings, films or fibers. They are particularly desirable for use as electrical insulation for electrical conductors.

These compositions can include mineral fillers such as carbonates including chalk, calcite and dolomite; silicates including mica, talc, wollastonite, silicon dioxide, glass spheres, glass powders; aluminum; clay; quartz; and the like. Also, reinforcing fibers such as fiberglass, carbon fibers, and the like may be used. The compositions may also include additives such as titanium dioxide; thermal stabilizers, ultraviolet light stabilizers, plasticizers, and the like.

EXAMPLES

The following examples provide specific illustrations of the present invention and are not to be construed in any way as a limitation on its scope or generality.

Sample Preparations and Test Procedures

There were two types of polymeric materials used in all the preparations of this invention; polybiphenylsulfone and bisphenol-S based polysulfone. The polybiphenylsulfone is a polymer having the repeat unit

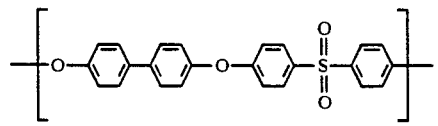

It is available commercially from Amoco Performance Products, Inc. under the trade name Radel R 5000. It has a reduced viscosity of approximately 0.60 dl/g as measured in N-methyl pyrrolidone at a concentration of 0.2 g/dl and 25° C. It has a number-average molecular weight of about 20,000 as measured by gel permeation chromatography using methylene chloride as a solvent and a polystyrene molecular weight calibration. This polymer is referred to hereafter as PSF-I.

One bisphenol-S polysulfone used is the commercial product Victrex 4100 G available from Imperial Chemical Industries, PLC. It is a polymer having the formula repeat unit

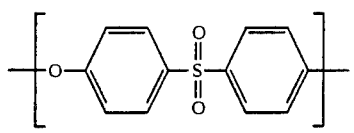

It has a reduced viscosity of about 0.50 g/dl in N-methylpyrrolidone at 25° C. and a concentration of 0.2 g/dl. Its number-average molecular weight by gel permeation chromatography is about 17,000 using methylene chloride as solvent and a polystyrene molecular weight calibration. This polymer is referred to hereafter as PES-I. The polymers were used in pellet form and all are transparent, by virtue of their amorphous character, and have a slight amber color.

Controls A and B

Two neat polymers PSF-I and PES-I were dried overnight in a Lydon dehumidified recirculating air oven at a temperature of 300° F. Parts were then injection molded on a Battenfeld injection molding machine with a 3 oz injection capacity to produce standard ASTM test specimens. Mechanical properties and heat deflection temperatures (HDT) were measured per the ASTM procedures shown below. All tests were conducted on $\frac{1}{8}$" thick specimens except HDT which was run on both $\frac{1}{8}$" and $\frac{1}{4}$" specimens.

| Property | ASTM Method No. |
| --- | --- |
| Tensile Modulus | D-638 |
| Tensile Strength | D-638 |
| Elongation at Break | D-638 |
| Notched Izod Impact Strength | D-256 |
| Tensile Impact Strength | D-1822 |
| Heat Deflection Temperature | D-648 |
| Flexural Modulus | D-790 |
| Flexural Strength | D-790 |

Examples 1 to 6

The compositions shown in Table I were mixed well as pellets and placed in a dehumidified air oven at 300° F. for about 16 hrs (overnight) for drying. The dry blends were then extruded using a 25 mm twin screw double vented Berstorff extruder having an L/D ratio of 33/1 according to the conditions profile shown in Table I. The first vent port was open to the atmosphere, the second was connected to a vacuum pump. The extruder was fitted with a double strand die. The polymer extrudate was pelletized after passing through a water trough for cooling. All blends were extruded and pelletized without incident at the throughput rates indicated in Table 1. Between successive blend compositions, two pounds of extrudate were designated as "transition" material and discarded. From past experience, this amount is sufficient to effectively displace the melt in the extruder so as the compositions of the final blends do not differ from those of the dry pellet mixes.

The six blends were dried again overnight in the Lydon oven at 300° F. and injection molded the following day on the Battenfeld injection molding machine described above to generate the needed ASTM parts. All blends appeared translucent on molding and the magnitude of the translucency increased towards the middle of the composition scale and became progressively less at the compositions rich in one polymer or the other. The lack of clarity in these blends is an indication of immiscibility between the two homopolymers.

Mechanical Properties

ASTM mechanical properties for the controls and blends are shown in Table II. The strength and modulus values for all blends appear to vary linearly with respect to PSF-I content in the blend. As a measure of ductility, elongation at break of all the blends can be considered equivalent to that of PSF-I within the variability of this measurement. The tensile impact, a discriminating test of polymer unnotched toughness is likewise similar for al compositions. All these mechanical properties confirm the very good mechanical compatibility of the blends of this invention. For compositions rich in PSF-I (examples 1, 2, and 3), little or no loss in the high notched Izod of PSF-I is observed. Accordingly, compositions comprising from 60 to 99 weight percent PSF-I and correspondingly from 1to 40 weight percent PES-I have many of the excellent physical properties of PSF-I.

Immiscible polymer blends which have poor mechanical compatibility are typically characterized by low strength for parts containing "weld lines" as a result of a multi-gated mold configuration. To ascertain the mechanical compatibility of these blends the weld-line strengths were measured against the base case with no weld line. ASTM tensile bars containing weld lines were produced on a Van Dorn injection molding machine fitted with a double gated tensile bar mold. Molding was performed at conditions similar to those used for the standard single gate case. Results are shown in Table III illustrating the retention of tensile strength over weld-line sections for all blends.

Steam Sterilization

To assess the steam sterilization resistance of the PSF-I/PES-I blend compositions, the following test was employed. 5"×$\frac{1}{2}$"×$\frac{1}{8}$" ASTM bars were mounted by fixing the bar horizontally from one end in a cantilever fashion, and a weight was suspended on the free end. The weight attached to the specimen was such that a maximum flexural stress of about 1000 psi was generated at the fixed end surface of the bar. The samples which were mounted side by side in a stainless steel drawer were then placed in a steam autoclave. The autoclave was operated at a steam pressure of 27 psig, and a temperature of 270° F., and the autoclave chamber was charged with water containing 50 part per million (ppm) morpholine. Each autoclave cycle consisted of a 5-minute heat-up and pressurization step followed by a hold at the set conditions for 30 minutes after which the autoclave was vented and allowed to cool down for 10 minutes. The samples were typically inspected at the completion of 15–25 cycles and all samples were tested in duplicates.

Table IV summarizes the results from the steam sterilization performance study. Quite unexpectedly, the performance of all blends except that of example 6 is comparable to that of PSF-I. None showed any evidence of stress cracking following 450 cycles of steam sterilization as described above. In comparison, PES-I experienced a rupture after only 45 cycles. The blend of example 6 had a rupture at 166 cycles-still significantly better than PES-I. The unbroken duplicate of example 6 and control B were cracked extensively and the test was not continued on them as they are also considered failures from the practical standpoint of the test. Accordingly, compositions comprising about 35 to 99 weight percent PSF-I and about 65 to 1 weight percent PES-I have improved resistance to steam containing amine stabilizers.

Chemical Resistance

The following test was performed to evaluate the resistance of the PSF-I/PES-I blend compositions to chemically induced stress cracking in the presence of an aqueous solution of a commercial wetting agent: Du-Dri which, available from Dubois Chemical. ASTM 5"×½"×⅛" specimens were retrained in flexure at a constant strain on brass bent bars of two different circular curvatures to generate nominal stresses of 2,000 and 4,000 psi, respectively. The exposed surface of the molded bars was then placed on contact with the solution by partially immersing the bars into a tray containing the solution. The Du-Dri was used at a concentration of 1.0 wt. % in water, and the test was conducted in an air oven at a temperature of 200° F. for a duration of 24 hrs. The samples were inspected for physical changes following this exposure and the results are shown in Table V. This data demonstrates compositions comprising 25 to 99 weight percent PSF-I and about 1 to 75 percent PSF-II have excellent chemical resistance.

TABLE I

Extrusion Conditions for Preparation of PSF-I/PES-I Blends of Example 1-6.*

| | Example | | | | | |
|---|---|---|---|---|---|---|
| | 1 | 2 | 3 | 4 | 5 | 6 |
| Percent PSF-I | 80 | 70 | 60 | 50 | 40 | 25 |
| Percent PES-I | 20 | 30 | 40 | 50 | 60 | 75 |
| Temperatures (C) | | | | | | |
| Zone 1 | 330 | 330 | 320 | 320 | 320 | 320 |
| Zone 2 | 340 | 340 | 330 | 330 | 330 | 330 |
| Zone 3 | 350 | 350 | 340 | 340 | 340 | 340 |
| Zone 4 | 350 | 350 | 350 | 340 | 340 | 340 |
| Zone 5 | 350 | 350 | 350 | 340 | 340 | 340 |
| Zone 6 | 360 | 350 | 350 | 340 | 340 | 340 |
| Zone 7 (Die) | 350 | 340 | 340 | 340 | 340 | 340 |
| Melt | 388 | 382 | 378 | 374 | 371 | 371 |

*Conditions common to all runs were approximately as follows:
screw speed = 200 rpm
throughput rate = 29 lbs/hr
Vent 2 vacuum reading = 30 in Hg
Vent 1 open to the atmosphere

TABLE II

Mechanical Properties of PSF-I, PES-I and 6 Blend Compositions of the Two Polymers.

| Example | PSF-I (%) | Tensile Strength (kpsi) | Tensile Modulus (kpsi) | Elongation at Break (%) | Flexural Strength (kpsi) | Flexural Modulus (kpsi) |
|---|---|---|---|---|---|---|
| Control A | 100 | 10.3 | 337 | 109 | 12.8 | 339 |
| 1 | 80 | 10.6 | 335 | 99 | 13.5 | 361 |
| 2 | 70 | 10.8 | 341 | 117 | 14.1 | 374 |
| 3 | 60 | 10.9 | 344 | 107 | 14.4 | 382 |
| 4 | 50 | 11.0 | 346 | 107 | 14.9 | 386 |
| 5 | 40 | 11.4 | 345 | 115 | 15.3 | 398 |
| 6 | 25 | 11.6 | 355 | 101 | 15.5 | 393 |
| Control B | 0 | 12.1 | 402 | 36 | 16.2 | 409 |

TABLE II-continued

Mechanical Properties of PSF-I, PES-I and 6 Blend Compositions of the Two Polymers.

| Example | PSF-I (%) | Notched Izod (ft-lb/in) | Tensile Impact (ft-lb/in²) | Heat Deflection Temp. [⅛"] (C) | Heat Deflection Temp. [¼"] (C) |
|---|---|---|---|---|---|
| Control A | 100 | 16.0 | 235 | 193 | 203 |
| 1 | 80 | 15.2 | 207 | 196 | 199 |
| 2 | 70 | 15.7 | 179 | 196 | 198 |
| 3 | 60 | 8.5 | 226 | 194 | 198 |
| 4 | 50 | 2.5 | 222 | 195 | 212 |
| 5 | 40 | 2.2 | 195 | 192 | 211 |
| 6 | 25 | 1.8 | 181 | 193 | 207 |
| Control B | 0 | 1.3 | 175 | 193 | 205 |

TABLE III

Weld Line Strengths of PSF-I/PES-I Blends Compared with the Strength of Non-weld Line Specimens.

| | | Tensile Strengths | |
|---|---|---|---|
| Example | PSF-I (%) | No Weld Line (kpsi) | Weld Line (kpsi) |
| Control A | 100 | 10.3 | 10.0 |
| 1 | 80 | 10.6 | 10.4 |
| 2 | 70 | 10.8 | 10.5 |
| 3 | 60 | 10.9 | 10.8 |
| 4 | 50 | 11.0 | 11.0 |
| 5 | 40 | 11.4 | 11.2 |
| 6 | 25 | 11.6 | 11.5 |

TABLE IV

Steam Sterilization* Performance of PSF-I, PES-I and 6 Blend Compositions of the Two Polymers.

| Example | PSF-I (%) | Number of Cycles Steam Sterilization | Observations |
|---|---|---|---|
| Control A | 100 | 450 | No Changes |
| 1 | 80 | 450 | No Changes |
| 2 | 70 | 450 | No Changes |
| 3 | 60 | 450 | No Changes |
| 4 | 50 | 450 | No Changes |
| 5 | 40 | 450 | No Changes |
| 6 | 25 | 166 | Cracks/Rupture |
| Control B | 0 | 45 | Cracks Rupture |

*Steam Sterilization Conditions: 1000 psi flexural stress, 27 psig steam with 50 ppm morpholine, 270 deg F steam, 30-minute autoclaving cycle.

TABLE V

Chemical Resistance* of PSF-I, PES-I and 6 Blend Compositions of the Two Polymers to Aqueous Du-Dri Wetting Solution.

| | PSF-I | Observation at Stress Level | |
|---|---|---|---|
| Example | (%) | 2,000 psi | 4,000 psi |
| Control A | 100 | No Changes | No Changes |
| 1 | 80 | No Changes | No Changes |
| 2 | 70 | No. Changes | No Changes |
| 3 | 60 | No. Changes | No Changes |
| 4 | 50 | No Changes | No Changes |
| 5 | 40 | No. Changes | No Changes |
| 6 | 25 | No Changes | No Changes |
| Control B | 0 | Edge Cracks | Rupture |

*Test Conditions: Exposure of 5" × ½" × ⅛" ASTM bars to 1.0% by weight solution at 200 deg F for 24 hrs. Flexural stress applied using constant-strain bent bars.

Essentially the same results can be obtained by replacing PES-I with Radel A-200 sold by Amoco Performance Products, Inc., which is the condensation product of dichlorodiphenyl sulfone with a 3:1 molar ratio of Bisphenol S to hydroquinone.

We claim:

1. A composition comprising (a) poly (biphenyl ether sulfone) consisting essentially of the repeating unit:

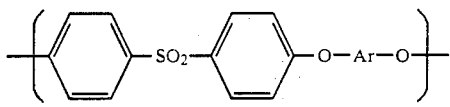

and (b) a second poly(aryl ether sulfone) consisting essentially of the repeating unit:

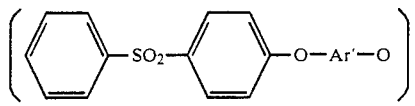

wherein Ar is a divalent group comprising at least 50 mole percent p-biphenylene and Ar' is a divalent group comprising at least 50 mole percent

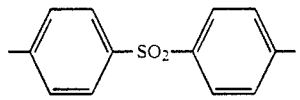

and the weight of (a) to (b) is from about 70 to 99 to 30 to 1.

2. The composition of claim 1 wherein Ar is a divalent group comprising at least 75 mole percent p-biphenylene.

3. The composition of claim 1 wherein Ar is p-biphenylene.

4. The composition of claim 1, wherein Ar consists essentially of biphenylene.

5. The composition of claim 1, wherein Ar' consists essentially of

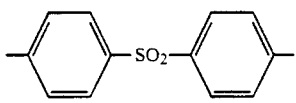

* * * * *

UNITED STATES PATENT AND TRADEMARK OFFICE
CERTIFICATE OF CORRECTION

PATENT NO. : 5,086,130
DATED : February 4, 1992
INVENTOR(S) : Dickinson, et al

It is certified that error appears in the above-identified patent and that said Letters Patent is hereby corrected as shown below:

| Col. | Line | |
|---|---|---|
| 2 | 37 | "materials , stress-cracked" should read --materials, stress-cracked-- . |
| 3 | 13 | "1 to 75 percent of weight of" should read --1 to 75 percent by weight of-- . |
| 4 | 4-5 | "4,4'-dichlorodiphenyl sulfone" should read --4,4'-diflourodiphenyl sulfone-- . |
| 5 | 23 | "secure the higher polymers" should read --secure the high polymers--· |
| 5 | 45 | "this invention ca be" should read --this invention can be-- . |
| 6 | 50-51 | "invention; polybiphonylsulfone" should read --invention: polybiphonylsulfone-- . |

Signed and Sealed this

Twentieth Day of July, 1993

Attest:

MICHAEL K. KIRK

Attesting Officer

Acting Commissioner of Patents and Trademarks